United States Patent [19]

Brophy et al.

[11] Patent Number: 4,665,270

[45] Date of Patent: May 12, 1987

[54] PROCESS FOR THE PRODUCTION OF HYDROCARBONS FROM HETERO-SUBSTITUTED ALKANES

[75] Inventors: John H. Brophy, Camberley; Josephus J. H. M. Font Freide, Weybridge; Jeremy D. Tomkinson, Staines, all of England

[73] Assignee: The British Petroleum Company, P.L.C., London, England

[21] Appl. No.: 752,182

[22] PCT Filed: Dec. 13, 1984

[86] PCT No.: PCT/GB84/00429

§ 371 Date: Jun. 28, 1985

§ 102(e) Date: Jun. 28, 1985

[87] PCT Pub. No.: WO85/02608

PCT Pub. Date: Jun. 20, 1985

[30] Foreign Application Priority Data

Dec. 16, 1983 [GB] United Kingdom .................. 8333613
Apr. 24, 1984 [GB] United Kingdom .................. 8410478
Jun. 12, 1984 [GB] United Kingdom .................. 8414934
Aug. 9, 1984 [GB] United Kingdom .................. 8420204

[51] Int. Cl.$^4$ ............................................. C07C 1/00

[52] U.S. Cl. .................................... 585/642; 585/408; 585/469; 585/733

[58] Field of Search ................ 585/408, 469, 642, 733

[56] References Cited

U.S. PATENT DOCUMENTS 2,425,861 8/1947 Brown et al. ...................... 585/642
3,894,107 8/1975 Butter et al. ...................... 585/408
4,497,968 2/1985 Wright et al. ...................... 585/304

Primary Examiner—Curtis R. Davis
Attorney, Agent, or Firm—Brooks Haidt Haffner & Delahunty

[57] ABSTRACT

A product comprising hydrocarbons having at least 2 carbon atoms is produced by contacting a monohalomethane at elevated temperature, e.g. 200° to 600° C., with a synthetic crystalline aluminosilicate zeolite having a silica to alumina molar ration of at least 12:1 and containing cations of either hydrogen, copper or a metal capable of forming an amphoteric oxide, which cations are introduced either by exchange and/or by deposition, provided that when the cation is hydrogen the zeolite is Theta-1. At temperatures below 330° C. the product predominantly comprises aliphatic hydrocarbons, of which a substantial proportion is isoalkanes and isoalkenes.

7 Claims, No Drawings

PROCESS FOR THE PRODUCTION OF HYDROCARBONS FROM HETERO-SUBSTITUTED ALKANES

The present invention relates to a process for the production of hydrocarbons from hetero-substituted alkanes.

The forecast longer-term shortage of petroleum has in recent years stimulated research into the production of chemicals and fuels from other raw materials. In particular both coal and natural gas, of which there are vast reserves, have been under consideration because both are readily converted by well established technology into a mixture of gases comprising carbon monoxide and hydrogen, conventionally referred to as synthesis gas, which in turn can be converted into methanol. Methanol is a useful intermediate for the production of valuable chemicals, for example acetic acid, ethanol, esters, acetic anhydride, etc., and in recent years its use has been proposed both as a gasoline blending component and as a feedstock for the production of liquid gasoline range hydrocarbons by conversion over synthetic crystalline aluminosilicate catalysts, see for example U.S. Pat. No. 4,138,442 (Mobil).

In U.S. Pat. No. 3,894,107 (Mobil) there is described a process for converting an aliphatic organic compound of the formula R-X where X is at least one of halogen, oxygen, sulphur or nitrogen to a product comprising a complex mixture of compounds including hydrocarbon compounds having a greater numer of carbon atoms than the organic compound reactant, a higher ratio of carbon atoms to heteroatoms than the organic compound reactant and a longest carbon to carbon chain length which is longer than the longest carbon chain length of the organic compound reactant by contacting the compound of formula R-X with a crystalline aluminosilicate zeolite having a silica to alumina ratio of at least about 12 and a constraint index of about 1 to 12. It is further stated that the zeolite may be in the hydrogen form or it may be base exchanged or impregnated to contain ammonium or a metal cation complement, of which the latter may be a cation of the metals of the Groups I through VIII of the Periodic Table. No specific cation-exchanged form of the zeolite is identified as being desirable for the conversion of any of the reactants embraced by the formula R-X, nor indeed is any specific cation-exchanged form of the zeolite said to be desirable for the conversion of compounds of the formula R-X as a generic class. The Examples illustrate only the use as catalyst of a zeolite in the hydrogen form and 24 of the 26 Examples are devoted to alkanol conversions, the remaining two being directed to methyl mercaptan conversion and tri-n-butylamine conversion. Of those Examples directed to alkanol conversion, the majority are devoted to the use of methanol as the feedstock.

U.S. Pat. No. 3,894,104 describes a process for converting a feed comprising compounds of the type $(R)_n$-X where R is a lower hydrocarbon moiety having 1 carbon atom, X is a hetero moiety selected from the group consisting of oxygen, hydroxyl, sulphur, nitrogen, halogen and cyanide and n is a number up to the valence of X, to other compounds having a higher ratio of R to X than in the feed by contacting such feed with a crystalline aluminosilicate zeolite catalyst, having a silica to alumina ratio of at least about 12 and a constraint index of about 1 to 12, at an elevated temperature of about 500° to about 750° F. at a space velocity of about 0.1 to 50 LHSV; the improvement, whereby a produce a product which is predominantly normally liquid hydrocarbon containing a larger proportion of aromatics, which comprises utilizing as said catalyst said zeolite which has been modified by the incorporation therewith of at least one metal of Groups Ib, IIa, IIb, IIIa, IVa and VIII of the Periodic Table. Representative feeds are said (column 5, lines 33 to 38) to include alcohols, particularly methanol, ethers, particularly dimethyl ether, ketones, particularly acetone and analogous and homologous materials such as mercaptans or amines, in admixture with each other and/or in admixture with other materials. The specific metals are incorporated in the catalyst for the purpose of increasing the aromatics content of the product. All 25 Examples are directed to the conversion of methanol.

An alternative approach to the conversion of methane, which forms the principal component of natural gas, to hydrocarbons in the gasoline boiling range is to convert the methane to monohalomethane and thereafter to catalytically convert same to hydrocarbons. This route is potentially more attractive than the methanol route because it eliminates one step in the process in that to produce the methanol feedstock the methane must first of all be converted to synthesis gas whereas methane can be converted directly with high selectivities to monohalomethane. Moreover, the hydrogen halide produced as a by-product of the monohalomethane conversion can be recycled to the monohalomethane production process, whereas the by-product of the methanol conversion process is not so utilisable. The chemistry of the conversion of methanol, and alcohols in general, as compared with monohalomethanes differs considerably, for example at low temperatures methanol is converted to dimethyl ether whereas this reaction is not possible for monohalomethanes. Another significant difference is that in the case of methanol conversion water is co-produced, whereas the conversion of monohalomethanes co-produces hydrogen halides which are known to dealuminate crystalline aluminosilicate zeolite structures leading to framework collapse and irreversible loss in catalytic activity. Dealumination would be anticipated to be more serious in the presence of hydrogen halides than in the presence of water. Conclusions drawn from the prior art regarding methanol conversion are therefore not necessarily applicable to monohalomethane conversions.

Japanese patent publication No. J55073-619 teaches that methane can be converted into methyl chloride and thereafter dehydrochlorinated using a zeolite to produce hydrocarbons having at least 2 carbon atoms. The zeolite employed is a silicate mineral consisting of $SiO_2$, $Al_2O_3$ and alkali metal or alkaline earth metal.

We have now found that monohalomethanes can be efficiently converted to hydrocarbons in the gasoline boiling range and moreover, within a certain temperature range, the selectivity to desirable aliphatic hydrocarbons and particularly to isoalkanes and isoalkenes can be high using cation-exchanged synthetic crystalline aluminosilicate catalysts. Furthermore, the activity of the catalyst depends on the nature of the zeolite employed and upon the nature of the cation. Moreover, we have surprisingly found that the activity of the catalysts can be maintained for substantial periods and that some at least of the catalysts can be regenerated.

Accordingly, the present invention provides a process for the conversion of a monohalomethane to a product comprising hydrocarbons having at least 2 carbon atoms which process comprises contacting the monohalomethane at elevated temperature with a synthetic crystalline aluminosilicate zeolite having a silicate to alumina molar ratio of at least 12:1 and containing cations of either hydrogen, copper or a metal capable of forming an amphoteric oxide, which cations are introduced either by exchange and/or by deposition, provided that when the cation is hydrogen the zeolite is Theta-1, as described and claimed in European Pat. No. 57049B.

As regards the monohalomethane, the halo-moiety may suitably be chloro- or bromo-, preferably chloro-. Mixtures of monohalomethanes and/or mixtures of monohalomethane with other monohaloalkanes, for example monohaloethane, may also be employed. The monohalomethanes may be used in substantially pure from or may be admixed with their polyhalogenated analogues or with inert diluents, nitrogen, hydrogen, oxygen, air, carbon oxides or hydrocarbons. As regards mixtures of polyhalogenated methanes and monohalomethanes, the amount of the polyhalogenated methane which can be tolerated in the mixture will depend upon the degree of halo-substitution, the nature of the zeolite and the nature of the cation. Thus, for example, using a mixture of monochloromethane and dichloromethane as the feed and a tin-exchanged ZSM-5 type crystalline aluminosilicate zeolite as catalyst, the maximum amount of dichloromethane which can be tolerated in the feed is about 40% v/v. It is of course preferred to operate with proportions of dihalomethane considerably less than the critical amount. Monohalomethanes may suitably be obtained by halogenation or oxyhalogenation of methane, or more preferably, methane in admixture with ethane and/or propane in the form, for example, of natural gas. Suitable processes for selectively producing monohalomethanes are described in our copending UK application publication No. 212024914 (BP Case No. 5350) and our copending European application publication No. 0117731 (BP Case No. 5538), the subject matter of which is incorporated by reference herein.

Any synthetic crystalline aluminosilicate zeolite having a silica to alumina molar ratio of at least 12:1, preferably from 15:1 to 150:1, even more preferably from 20:1 to 100:1, may be employed. Suitable synthetic crystalline aluminosilicate zeolites include Theta-1 as described in EP-A-No. 57049; ZSM-4 as described in UK Pat. Nos. 1,117,568; 1,227,294; 1,297,256; and 1,321,460; ZSM-11 as described in U.S. Pat. No. 3,709,979; ZSM-5/ZSM-11 as described in U.S. Pat. No. 4,229,422; ZSM-35 as described in U.S. Pat. No. 4,016,245; ZSM-34 and zeolite Nu-1 as described in GB-A-No. 1,559,367. Preferred synthetic crystalline aluminosilicates are those designated as MFI zeolites in the atlas of Zeolite Structure Types by W. M. Meier and D. H. Olson, published by the Structure Commission of the International Zeolite Association and Theta-1. Specific MFI-type zeolites which may be used and processes for their production are described in for example U.S. Pat. Nos. 3,702,886; 3,709,979; 4,205,053; 4,166,099; 4,139,600 and 4,151,189; UK Pat. Nos. 1,365,318 and 1,567,948 and EP-A-Nos. 2899 and 2900, all of which utilise an organic base in their preparation. Alternatively, MFI-type zeolites may be synthesised from gels which are free from organic bases as described in for example EP-A-No. 30911, U.S. Pat. No. 4,199,556 and GB-A-No. 2,018,232.

The crystalline aluminosilicate designated Theta-1 has the following composition in term of the mole ratios of the oxides:

$$0.9 \pm 0.2 M_{2/n}O : Al_2O_3 : xSiO_2 : yH_2O$$

where M is at least one cation having a valence n, x is at least 12 and y/x is between 0 and 25, said aluminosilicates in the calcined hydrogen-form having an X-ray diffraction pattern as set forth in Table A hereinafter.

TABLE A

| 2 theta | d-spacing | Relative intensity 100 × I/I$_o$ |
|---|---|---|
| 8.15 ± 0.5 | 11.5–10.2 | 50 to 100 |
| 10.16 ± 0.5 | 8.29–9.14 | 5 to 25 |
| 12.77 ± 0.5 | 7.20–6.66 | 10 to 20 |
| 16.36 ± 0.5 | 5.58–5.25 | 5 to 15 |
| 19.42 ± 0.5 | 4.68–4.45 | 5 to 15 |
| 20.35 ± 0.5 | 4.47–4.26 | 50 to 100 |
| 24.22 ± 0.5 | 3.75–3.60 | 50 to 100 |
| 24.65 ± 0.5 | 3.68–3.54 | 30 to 90 |
| 25.75 ± 0.5 | 3.52–3.39 | 15 to 45 |
| 35.63 ± 0.5 | 2.55–2.48 | 15 to 40 | scanned up to 2 theta = 36.

The aluminosilicate may suitably be prepared by forming a mixture of all the reactants, by simply mixing them together while maintaining the mixture suitably at a temperature between 0° and 100° C., preferably between 20° and 60° C., until a homogeneous gel is formed and crystallising the mixture so-formed at a temperature above 70° C., preferably between 100° and 220° C., for a period of at least 2 hours, preferably for from 6 to 240 hours. Further details regarding the crystalline aluminosilicate and its method of preparation may be found in the aforesaid European Pat. No. 0057049, which is incorporated by reference in this specification.

As prepared the aforementioned crystalline aluminosilicate will almost certainly contain cations other than those associated with their crystal structures, for example they may contain either alkali metal and/or alkaline earth metal cations, organic nitrogen cations or ammonium cations and possibly they may also contain organic bases or acids deposited in the pores and on the surface thereof, depending on their method of preparation. In order to produce catalysts which are active in the process of the present invention it is necessary either to exchange some or all of the exchangeable cations of the crystalline aluminosilicates as prepared with other cations and/or deposit cations thereon.

Using zeolites other than Theta-1, activating cations are cations of copper or of metals capable of forming an amphoteric oxide, an amphoteric oxide being regarded in simple terms as an oxide which exhibits both acidic and basic properties. Metals capable of forming amphoteric oxides include for example beryllium, titanium, zirconium, hafnium, iron, cobalt, rhodium, silver, gold, zinc, aluminium, gallium, indium, silicon, germanium, tin, lead, pollonium and uranium. Of the aforesaid metals, zinc, gallium and silver are preferred at lower temperatures, for example 200° to 260° C. Although Theta-1 may be activated with at least one of the aforesaid cations, it is preferred to activate the Theta-1 zeolite with hydrogen ions. We have found that the hydrogen form of Theta-1 is a more active catalyst than the hydrogen form of the MFI zeolite.

Cation-exchange may be accomplished using conventional ion-exchange techniques. Deposition of the cation(s) may be accomplished by impregnation or precipitation, or by any other technique. Deposition is preferably effected by impregnation with a solution of a suitable compound, for example a metal salt, which almost inevitably is accompanied by exchange of exchangeable cations with other cations. Using cation-exchange, it is preferred to exchange substantially all the original exchangeable cations. Using deposition the amount of metal or metals deposited may suitably be up to 25% w/w, preferably from 0.1 to 15% w/w calculated as metal(s) and based on the total weight of the catalyst.

It is preferred to calcine the crystalline aluminosilicate after introduction of the replacing cations and optionally also before introduction of the replacing cations. Calcination may suitably be effected by heating, suitably in a stream of air, oxygen, inert gas or hydrogen, or any combination thereof at a temperature in the range from 200° to 600° C., or above, for at least 0.5 hr.

The process for the conversion of monohaloalkane to hydrocarbons may suitably be effected at an elevated temperature in the range from 80° to 600° C. The pressure may suitably be atmospheric pressure, though higher and lower pressures may be employed if desired. Within the temperature range 80° to 600° C., aromatic hydrocarbons are not formed in significant proportions below about 330° C. Below 330° C., monohalomethanes are converted to a hydrocarbon product predominantly comprising aliphatic hydrocarbons and, surprisingly, it is found that a substantial proportion of the aliphatic hydrocarbons are isoalkanes and isoalkenes, which are highly desirable components of chemicals feedstocks and gasoline blending additives. It is preferred, for the production of aliphatic hydrocarbons, to operate in the temperature range 200° to 330° C., for example from 200° to 260° C. It may be noted by way of contrast that in the temperature range 200° to 260° C. and even higher, for example 327° C., methanol would be converted to dimethyl ether.

Although the process may be operated batchwise, it is preferably operated in a continuous manner. The Gas Hourly Space Velocity (GHSV) defined as the volume of reactant gas at STP per volume of catalyst per hour for continuous operation may suitably be in the range from 1 to 10,000 vol/vol/hour. The process, may for example, fit into a process scheme whereby methane, optionally admixed with ethane and/or propane, is fed to a first zone wherein it is halogenated and/or oxyhalogenated to produce monohalomethane at a selectivity based on methane fed of greater than about 80%, the monohalomethane and any monohaloethane and/or monohalopropane so-produced is separated and passed as feed to the process of the present invention and thereafter the hydrocarbon product is separated from the co-produced hydrogen halide(s), the hydrogen halide(s) either being recycled to the oxyhalogenation or being oxidised and the halogen(s) so-produced being recycled to the halogenation.

The catalyst in the process of the present invention may be employed in the form of a fixed bed or a fluidised bed.

The process of the present invention will now be further illustrated by reference to the following Examples.

In a number of the Examples the terms "iso-content" and "aliphatic content" will be employed. The term "iso-content" is an indication of the minimal molar amount (%) of isoalkanes/isoalkenes present as part of the total $C_4$–$C_{11}$ aliphatic hydrocarbon content. The term "aliphatic content" refers, on a similar basis, to the minimal amount of aliphatic hydrocarbons present in the total $C_3$–$C_{14}$ aliphatic and aromatic hydrocarbon product composition. The "Al/Ar" ratio refers to the ratio of selectivities of $C_2^+$-aliphatic to $C_6^+$-aromatic hydrocarbons. These are terms defined in a manner such as to give a clear indication of the variation in product spectra.

EXAMPLES 1 TO 4

Monochloromethane was fed continuously to a reactor containing the cation-exchanged form specified in Table 1 of the synthetic crystalline aluminosilicate zeolite ZSM-5 having a silica to alumina molar ratio of 41:1. The reactor was heated externally by means of an electric furnace and the heated zone was maintained at the temperature specified. The applied GHSV in per hourly units as STP are shown in Table 1. The product stream was analysed by on-line gas chromatography.

The composition of the product streams, excluding unreacted monohalomethane and hydrogen chloride, are shown in Table 1 together with a summary of experimental details.

With reference to Table 1, no aromatic hydrocarbons were obtained using the metal cation-exchanged form of the ZSM-5 zeolite under the conditions of the experiments. The aliphatic hydrocarbon product had a high iso-content.

Comparison Test A

The procedure of Examples 1 to 4 was repeated using the hydrogen form of the ZSTM-5 zeolite as used in Examples 1 to 4 and using the specific conditions shown in Table 1.

This is not an example according to the invention because the hydrogen form of the zeolite was employed. It demonstrates that under the conditions of the experiment lower conversions are obtained using the hydrogen form of the zeolite.

Comparison Test B

The procedures of Examples 1 to 4 was repeated using the hydrogen form of the ZSM-5 zeolite back-exchanged with sodium cations (15%) and using methanol as the feed in place of monochloromethane at a comparable Liquid Hourly Space Velocity. The major product (91% conversion) was dimethyl ether.

This is not an Example according to the present invention because methanol and not a monohalomethane was used as feed. It is provided for the purpose of highlighting the difference in chemical terms between monohaloalkanes and alkanols. Under the conditions employed, methanol forms mainly its condensation adduct, dimethyl ether, and small amounts of $C_2$–$C_3$ hydrocarbons, whereas monochloromethane forms mainly $C_4$–$C_{11}$ aliphatic hydrocarbons.

EXAMPLES 5 TO 13

The procedure of Examples 1 to 4 was repeated using the conditions and the cation-exchanged form specified in Table 2 of the ZSM-5 zeolite as used in Examples 1 to 4.

The composition of the product streams, excluding unreacted monochloromethane and hydrogen chloride, are shown in Table 2 together with a summary of experimental details.

It can be seen from Table 2 that operation at the higher temperatures increases the monochloromethane conversions, whilst producing a highly aliphatic hydrocarbon product containing a high proportion of iso-hydrocarbons. The Al/Ar ratio in, for example, Examples 6 and 10 was respectively 6.4 and 7.6 indicating a high aliphatic content of the product stream. Under similar conditions with methanol as feed (327° C.; 1 h$^{-1}$ WHSV) over the sodium-exchanged zeolite (88% exchange) only low conversion (1%) to hydrocarbon products was observed, the bulk of the product (94% conversion) being dimethyl ether.

In the case of Example 5 (Cu-exchanged form) the monochloromethane conversion declined (to 70% conversion) after 18 hours on stream. This compares with a drop in conversion (from 89% to 24%) after 9 hours on stream using the hydrogen form of the zeolite (327° C.; 200 h$^{-1}$) and is an indication of the improved stability of the catalysts of the present invention. Furthermore, the activity of the Cu-exchanged zeolite was restored to its original value by regeneration, whereas this was not the case for the hydrogen-exchanged zeolite.

EXAMPLES 14 TO 19

The procedure of Examples 1 to 4 was repeated using the feed compositions and cations as shown in Table 3.

The composition of the product streams, excluding unreacted methyl chloride and hydrogen chloride, are shown in Table 4 together with a summary of experimental details.

Comparison Tests C and D

The procedure of Examples 1 to 4 was repeated using the feed compositions and cations as shown in Table 3.

The composition of the product streams, excluding unreacted haloalkane and hydrogen chloride, are shown in Table 4, together with a summary of experimental details.

These are not Examples according to the invention and are included for the purpose of demonstrating that when the dichloromethane content of the feed mixture is greater than about 40% v/v hardly any conversion to higher hydrocarbons is obtained.

EXAMPLES 20 TO 24

The procedure of Examples 1 to 4 was repeated using, in place of the cation-exchanged ZSM-5 zeolite as used in those Examples, various cation-exchanged forms, as specified in Table 5, of a Theta-1 zeolite prepared as described in the aforesaid European Pat. No. 57049B.

The composition of the product streams, excluding unreacted monochloromethane and hydrogen chloride are shown in Table 5 together with a summary of experimental details. In Table 5 is included the corresponding data for Comparison Test A, for comparison purposes.

TABLE 1

|  | Example | | | | Comp. Test A | Comp. Test B |
|---|---|---|---|---|---|---|
|  | 1 | 2 | 3 | 4 | | |
| Aliphatics | | | | | | |
| C$_1$ | 3 | 2 | 3 | 1 | 0 | |
| C$_2$'s | trace | 1 | 0 | 1 | 0 | 43 |
| C$_3$'s | 23 | 11 | 11 | 14 | 8 | 29 |
| C$_4$'s | 56 | 60 | 67 | 64 | 68 | 14 |
| C$_5$'s–C$_{11}$'s | 18 | 26 | 19 | 20 | 24 | 14 |
| Aromatics | | | | | | |
| C$_6$–C$_{14}$'s | 0 | 0 | 0 | 0 | 0 | 0 |
| Conversion | 60 | 21 | 9 | 24 | 7 | 9$^b$ |
| Zeolite Form | Zn | Ag | Sn | Ga | H | Na |
| Temp/°C. | 227 | 227 | 227 | 227 | 227 | 224 |
| GHSV/h$^{-1}$ | 55 | 73 | 52 | 51 | 57 | 1$^a$ |
| iso-content | 80 | 87 | 92 | 85 | 100 | 82 |
| aliphatic content | 100 | 100 | 100 | 100 | 100 | 100 |

Note
$^a$ = Liquid Hourly Space Velocity
$^b$ = Additional 91% conversion to dimethyl ether

TABLE 2

|  | Example | | | | | | | | |
|---|---|---|---|---|---|---|---|---|---|
|  | 5 | 6 | 7 | 8 | 9 | 10 | 11 | 12 | 13 |
| Aliphatics | | | | | | | | | |
| C$_1$ | 3 | 3 | 3 | 2 | 3 | 1 | 1 | 5 | 5 |
| C$_2$'s | 3 | 3 | 3 | 3 | 6 | 2 | 2 | 5 | 5 |
| C$_3$'s | 53 | 60 | 69 | 59 | 50 | 66 | 66 | 59 | 60 |
| C$_4$'s | 18 | 16 | 7 | 14 | 20 | 18 | 11 | 11 | 12 |
| C$_5$'s–C$_{11}$'s | 3 | 13 | trace | 2 | 5 | 3 | 2 | 2 | 1 |
| Aromatics | | | | | | | | | |
| C$_6$–C$_{14}$'s | 20 | 5 | 18 | 20 | 16 | 10 | 18 | 18 | 17 |
| Conversion | 97 | 95 | 100 | 96 | 73 | 92 | 99 | 98 | 99 |
| Zeolite Form | Cu | Ag | Sn | Sn | Ti | Ga | Ga | Cu | Ti |
| Temp/°C. | 327 | 327 | 327 | 327 | 327 | 327 | 327 | 377 | 377 |
| GHSV/h$^{-1}$ | 111 | 85 | 60 | 211 | 200 | 50 | 64 | 327 | 200 |
| iso-content | 52 | 59 | 42 | 43 | 45 | 43 | 44 | 46 | 39 |
| aliphatic content | 79 | 95 | 81 | 84 | 82 | 93 | 85 | 80 | 81 |

TABLE 3

| | FEED COMPOSITION (% v/v) | | | | | |
|---|---|---|---|---|---|---|
| Example | monochloro-methane | monobromo-methane | dichloro-methane | monochloro-ethane | nitrogen | hydrogen |
| 14 | 70 | — | — | 30 | — | — |
| 15 | — | 100 | — | — | — | — |
| 16 | 50 | — | — | — | — | 50 |
| 17 | 96 | — | 4 | — | — | — |
| 18 | 91 | — | 9 | — | — | — |
| 19 | 82 | — | 18 | — | — | — |
| Comp Test C | 57 | — | 43 | — | — | — |
| Comp | — | — | 18 | — | 82 | — |

TABLE 3-continued

| | FEED COMPOSITION (% v/v) | | | | | |
|---|---|---|---|---|---|---|
| Example | monochloro-methane | monobromo-methane | dichloro-methane | monochlo-roethane | nitrogen | hydrogen |
| Test D | | | | | | |

TABLE 4

| | Example | | | | | | | |
|---|---|---|---|---|---|---|---|---|
| | 14 | 15 | 16 | 17 | 18 | 19 | C | D |
| Aliphatics | | | | | | | | |
| $C_1$ | 1 | 3 | 2 | 6 | 2 | 2 | — | — |
| $C_2$'s | 4 | 8 | 4 | 6 | 3 | 3 | — | — |
| $C_3$'s | 49 | 55 | 73 | 78 | 77 | 69 | — | — |
| $C_4$'s | 24 | 15 | 16 | 5 | 10 | 11 | — | — |
| $C_5$'s–$C_{11}$'s | 5 | 3 | 2 | 0 | 0 | 1 | — | — |
| Aromatics | | | | | | | | |
| $C_6$–$C_{14}$'s | 16 | 16 | 3 | 5 | 8 | 14 | — | — |
| Conversion | 85 | 58 | 94 | 96 | 99 | 93 | 0 | 0 |
| Zeolite Form | Ga | Ga | Sn | Sn | Sn | Sn | Sn | Sn |
| Temp/°C. | 327 | 327 | 327 | 327 | 327 | 327 | 327 | 327 |
| GHSV/$h^{-1}$ | 170 | 200 | 258 | 64 | 61 | 214 | 177 | 217 |

TABLE 5

| | EXAMPLE | | | | | |
|---|---|---|---|---|---|---|
| PRODUCT | 20 | Comp Test A | 21 | 22 | 23 | 24 |
| Aliphatics | | | | | | |
| $C_1$ | 29.9 | trace | 36.8 | 20.6 | 14.5 | 35.4 |
| $C_2$'s | 6.0 | trace | 22.3 | 14.4 | 22.6 | 13.0 |
| $C_3$'s | 20.8 | 7.6 | 28.0 | 36.0 | 40.0 | 35.2 |
| $C_4$'s | 33.3 | 68.2 | 4.8 | 20.1 | 15.1 | 11.4 |
| $C_5$–$C_8$'s | 10.0 | 24.1 | 4.7 | 8.9 | 7.7 | 5.0 |
| Monochloroethane | 0 | 0 | 3.0 | | | |
| % Monochloromethane conversion | 42 | 7 | 52 | 23 | 58 | 77 |
| Zeolite type | Theta-1 | ZSM-5 | Theta-1 | Theta-1 | Theta-1 | Theta-1 |
| Form | Hydrogen | Hydrogen | Hydrogen | zinc | tin | titanium |
| Temperature (°C.) | 227 | 227 | 500 | 327 | 377 | 377 |
| GHSV ($h^{-1}$) | 37 | 57 | 80 | 38 | 43 | 40 |

We claim:

1. A process for the conversion of a monohalomethaane to a product comprising hydrocarbons having at least 2 carbon atoms which process comprises contacting the monohalomethane at elevated temperature with a synthetic crystalline aluminosilicate zeolite having a silica to alumina molar ratio of at least 12:1 and containing cations of hydrogen ions, which cations are introduced either by exchange and/or deposition, and wherein the zeolite is Theta-1.

2. A process according to claim 1 wherein the elevated temperature is in the range 80° to 600° C.

3. A process according to claim 2 wherein the temperature is below about 330° C. and the hydrocarbon product predominantly comprises aliphatic hydrocarbons.

4. A process according to claim 3 wherein the temperature is in the range 200° to 330° C.

5. A process according to claim 1 wherein the monohalomethane is obtained by halogenation or oxyhalogenation of methane in admixture with ethane and/or propane.

6. A process according to claim 1 wherein the monohalomethane is monochloromethane.

7. A process according to claim 4, wherein the temperature is in the range of 200° to 260° C.

* * * * *

UNITED STATES PATENT AND TRADEMARK OFFICE
CERTIFICATE OF CORRECTION

PATENT NO. : 4,665,270
DATED : May 12, 1987
INVENTOR(S) : John Howard Brophy et al It is certified that error appears in the above-identified patent and that said Letters Patent is hereby corrected as shown below:

Col. 2, line 2, "whereby a" should read -- whereby to --

Col. 3, line 4, "a silicate" should read -- a silica --

Col. 6, line 32 "ZSTM-5" should read -- ZSM-5 --

Col. 6, line 42 "procedures" should read -- procedure --

Col. 9, line 42-43 "monohalomethaane" should read
-- monohalomethane --

Signed and Sealed this

Twenty-seventh Day of October, 1987

Attest:

DONALD J. QUIGG

Attesting Officer     Commissioner of Patents and Trademarks